United States Patent [19]

Sale et al.

[11] Patent Number: 5,927,977
[45] Date of Patent: Jul. 27, 1999

[54] DENTAL SCALER

[75] Inventors: David William Sale, Heber Springs; Ronald W. Haynes, Shirley; Elbert L. Young, Jr., Searcy, all of Ark.

[73] Assignee: Professional Dental Technologies, Inc., Batesville, Ark.

[21] Appl. No.: 08/977,592

[22] Filed: Nov. 25, 1997

Related U.S. Application Data

[60] Provisional application No. 60/031,928, Nov. 27, 1996.

[51] Int. Cl.[6] .................................................. A61C 1/07
[52] U.S. Cl. ............................ 433/86; 433/32; 433/80; 433/119; 433/126
[58] Field of Search ........................... 433/86, 80, 82, 433/84, 98, 101, 32, 126, 119

[56] References Cited

U.S. PATENT DOCUMENTS

| | | | |
|---|---|---|---|
| 3,924,335 | 12/1975 | Balamuth et al. | 433/119 |
| 4,493,695 | 1/1985 | Cook | 433/84 |
| 4,589,847 | 5/1986 | Loge et al. | 433/126 |
| 5,338,194 | 8/1994 | Strohmaier | 433/84 |
| 5,419,703 | 5/1995 | Warrin et al. | 433/86 |
| 5,626,472 | 5/1997 | Pennetta | 433/80 |
| 5,716,580 | 2/1998 | McFerrin | 433/80 |

FOREIGN PATENT DOCUMENTS

0 323 598 A2  12/1988  European Pat. Off. .

Primary Examiner—John J. Wilson
Attorney, Agent, or Firm—Nims, Howes, Collison, Hansen & Lackert

[57] ABSTRACT

A dental scaling system includes a scaling instrument with a handpiece and a scaling tip at the end of the handpiece. An ultrasonic transducer is connected to the scaling tip, and there is an irrigant outlet in the scaling tip. A cable is attachable to the handpiece and includes an irrigant passage and two lead wires for supplying irrigant and electrical energy to the handpiece. An irrigant supply bottle is releasably attachable on a housing, and the cable is attachable on the housing. The housing includes an air pump to pressurize and transfer irrigant liquid from the irrigant supply bottle through the cable to the handpiece. The housing also includes electronics to power and control the ultrasonic transducer. Each irrigant supply bottle includes a mounting member with a pair of wings, received in a forked docking assembly on the housing, with the mounting member lockable in the docking assembly.

119 Claims, 8 Drawing Sheets

DENTAL SCALER

CROSS REFERENCE TO RELATED APPLICATION

This application claims the benefit of U.S. provisional application Ser. No. 60/031,928 filed Nov. 27, 1996.

TECHNICAL FIELD

This invention relates to electronic dental scalers and more particularly to electronic dental scalers having a dedicated and integral irrigation supply, a slim handpiece design and means for alerting a user to scaler tip wear.

BACKGROUND

A dental scaler is an instrument which relies on an angled tip to remove plaque and other deposits from dental tooth surfaces. One type of scaler relies on an ultrasonic generator to impart vibration to the tip to enhance the removal process. The tip further includes a passage for delivering a small amount of water to an opening in an end of the tip which provides cooling of the tooth surface at the point of cleaning.

Various electronic scalers are known in the art. However, these suffer from various deficiencies. First, a separate irrigation device is typically required to provide a larger water flow, which requires the user to switch between instruments. Irrigation devices generally utilize direct line connections to plumbed water sources, which, because of hygienic concerns, requires plumbing connections with provisions to prevent back flow into the water supply. Another disadvantage is that the typical scaler handpiece is fairly large and complex, because it requires water and electrical connections that must retain their integrity through numerous cycles as the handpiece, for sanitary reasons, must routinely be removed and autoclaved.

Another problem with existing dental scalers is the change in cleaning effectiveness with increasing wear of the tip. At present, there is no way to accurately assess this wear as a tip may visibly appear to be adequate while its ultrasonic properties and vibratory response are not.

Consequently, an improved dental scaler is needed to address these problems and offer solutions and improvements.

SUMMARY OF THE INVENTION

It is an object of the present invention to provide a dental scaler handpiece that is slim, having a simplified design which is easier for the user to maneuver in the mouth.

It is a further object to provide a dental scaler with a self contained irrigant for increased portability, and to avoid costly plumbing modifications.

It is yet another object to provide a dental scaler which is capable of delivering irrigants as well as medicaments in the mouth.

It is yet another object to provide electronic monitoring of tip function to alert the user when a tip must be replaced.

These and other objects of the present invention are achieved by a dental scaling system comprising a scaling handpiece having a scaling tip at a first end thereof, an ultrasonic transducer in the handpiece, connected to the scaling tip, an irrigant passage passing through the handpiece to an outlet on the scaling tip, flexible connection means for connecting the handpiece to an irrigant supply and the ultrasonic transducer to a power supply, the connection means including an irrigant passage extending therethrough, a housing, a first end of the connection means engaged to the housing, the housing incorporating the irrigant supply and means for transferring irrigant from the irrigant supply to the handpiece.

Preferably, the handpiece irrigant passage substitutes for an electrical wire in the handpiece, thereby simplifying the design and reducing the overall size of the handpiece. In addition, optional means for heating the irrigant are included in the handpiece for heating the irrigant as it passes therethrough to increase patient comfort. Also, the use of a separate, dedicated but independent irrigant supply avoids complex plumbing connections and allows supplying medicaments as well as irrigant in the mouth. Electronic monitoring means are utilized to monitor tip vibratory response and to issue an alert when the tip should be replaced.

DETAILED DESCRIPTION OF THE INVENTION

Figure 1:
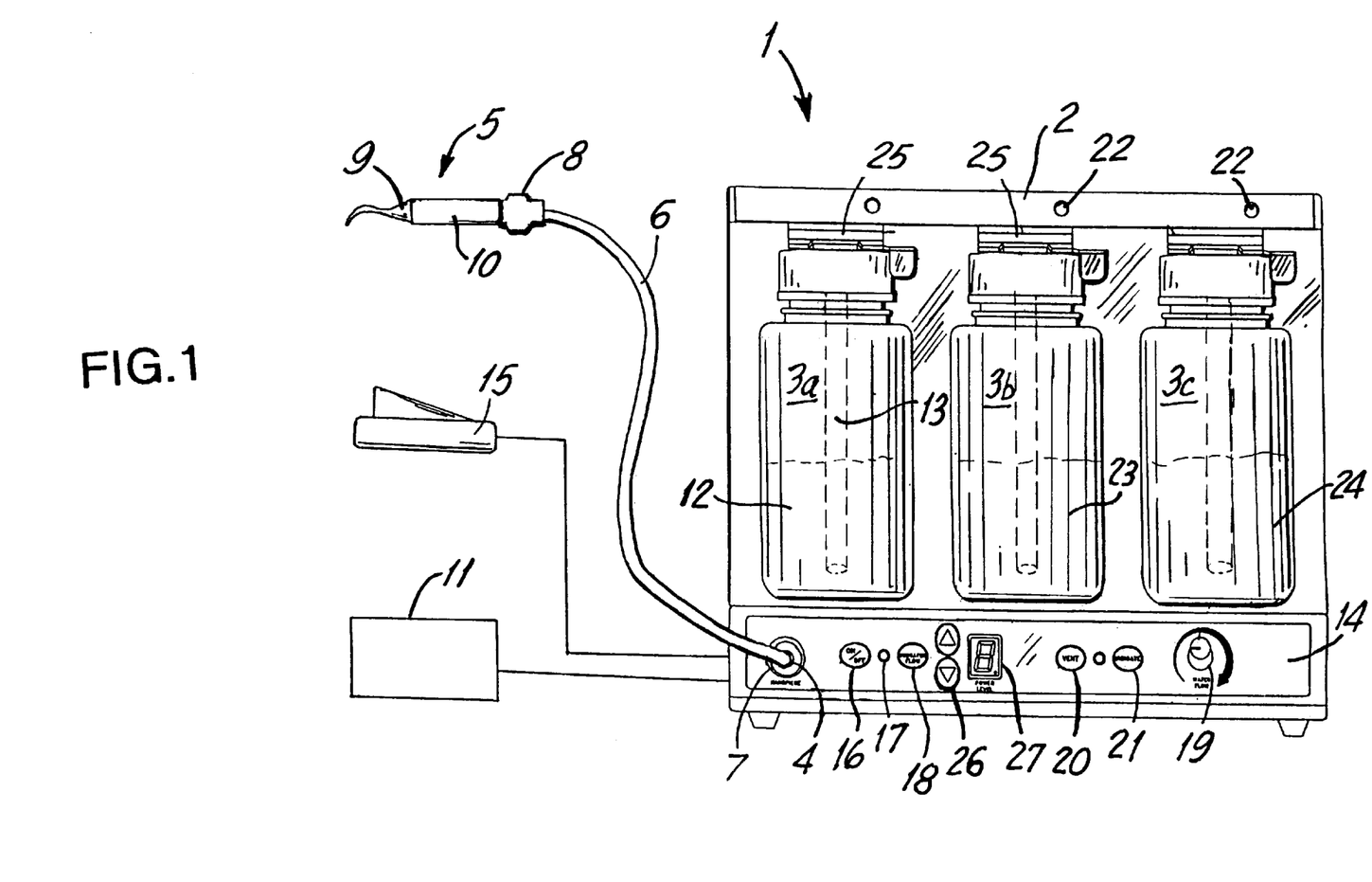
FIG. 1 is a schematic view of a dental scaling system in accordance with the present invention.

Referring to FIG. 1, a dental scaler system 1 includes a housing 2 on which irrigant bottles 3 are removably mounted. The housing 2 includes a connector 4 which attaches to a dental scaler instrument 5 by means of a flexible cable 6. The flexible cable 6 has a pair of resilient connector boots 7 and 8 at opposite ends thereof, which slip onto the connector 4 and the instrument 5. The scaler instrument 5 includes a scaler tip 9 and a handpiece 10. The scaler tip 9 is vibrated by an ultrasonic transducer located inside the handpiece 10. The dental scaler system 1 is powered via a low voltage electrical power transformer 11 which connects to common house current.

The housing 2 includes an electronics package (not shown) for controlling the ultrasonic transducer in the scaler instrument 5, which will be discussed below. Means (not shown) are located in the housing for driving an irrigant 12 from the selected buttle 3, through a dip tube 13, through the cable 6 to the tip 9 of the scaler instrument 5. Preferably, air pressure is used to drive the irrigant through the cable. A control panel 14 is located on a front surface of the housing 2, and there is also a foot pedal 15 connected to the housing 2 for ease in actuating the scaler.

The control panel 14 includes a master power switch 16, and a power indicator light 17. A control switch 18 is used to turn the irrigation on and off, with the rate of irrigant flow controlled by a twist knob 19. The irrigant bottles 3 are vented when a button 20 is pressed to reduce pressure after the procedure is completed to allow the irrigant to flow back to the bottle so as to prevent dripping during disconnection of the handpiece from the cable. The irrigant bottle in use is selected by pressing an irrigant bottle selector button 21. Indicator lights 22 located over the bottles 3 indicate which of the irrigant bottles is in use. A practitioner, by pressing the irrigant selector button 21, may select between, for example, one bottle 3b containing water 23 and another bottle 3c containing a medicament 24. For purpose of this application, the term "irrigant" will include liquids such as water, liquid medicaments, and combination thereof Each of the bottles is releasably attached to the housing 2 via a docking assembly 25. The level of energy supplied to the ultrasonic transducer is adjusted using up/down buttons 26 and this level is indicated on a display 27. Irrigant or ultrasonic energy are supplied to the scaler tip 9 only when the foot pedal 15 is depressed, freeing a practitioner's hands for other tasks.

Figure 2A:
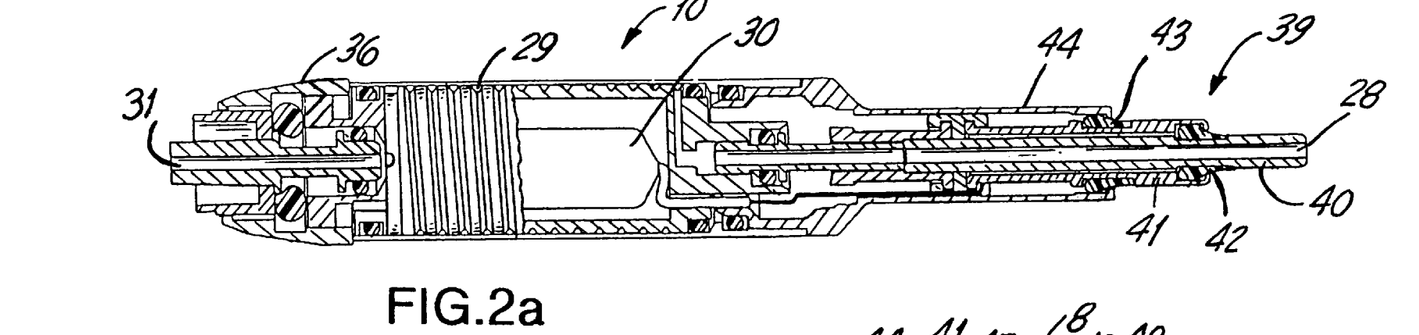
FIG. 2a is a cross-sectional illustration of a dental scaler handpiece in accordance with the present invention.
Figure 2B:
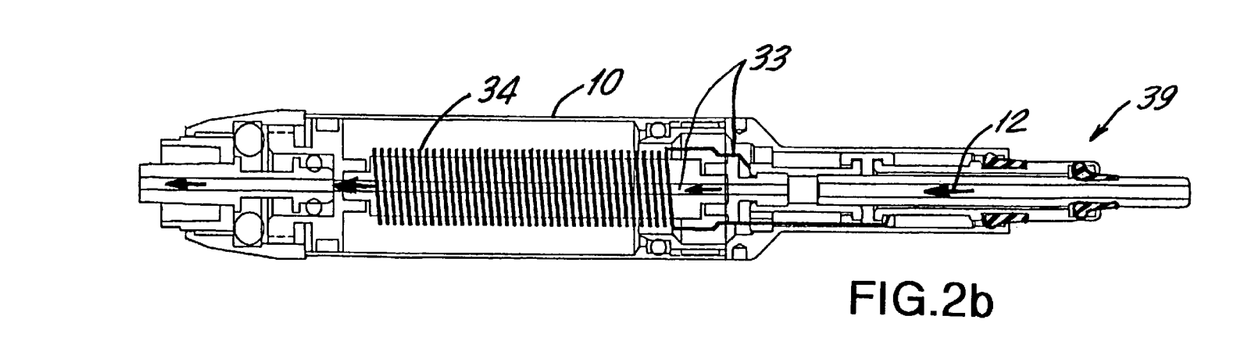
FIG. 2b is a cross-sectional illustration of an alternative heating element used in the dental scaler handpiece.

The dental scaling system of the invention contemplates use of a dedicated scaling instrument with irrigant supplied as a lubricant or tooth surface coolant, though without irrigant heating, or use of a dedicated irrigator, with or without heating of the liquid passing therethrough, or use of an instrument that provides both scaling and irrigator functions, and includes an irrigant heater. Such handpieces are readily interchangeable in accordance with the present invention A cross section of a dental irrigation handpiece 10 with the tip removed is illustrated in FIG. 2a. Irrigant 12 flows into the handpiece 10 through an axial irrigant inlet channel 28. The irrigant liquid then travels through a spiral path 29 surrounding a heating element 30. After being heated to a comfortable temperature, the irrigant flows out of the handpiece 10 through a forward axial irrigant channel 3. A tip 9a attached to the forward end of the handpiece would have a corresponding channel 32 for delivery of the fluid to an end of the tip, as shown in FIG. 2d. Such a tip provides assurance that irrigant or medicament is delivered to selected areas and surfaces in the mouth. In an alternative arrangement shown in FIG. 2b, the irrigant travels through an axial passage which extends along the entire length of the scaler handpiece, and the axial passage 33 has a heating element 34 coiled over at least a portion of its length.

Figure 2C:
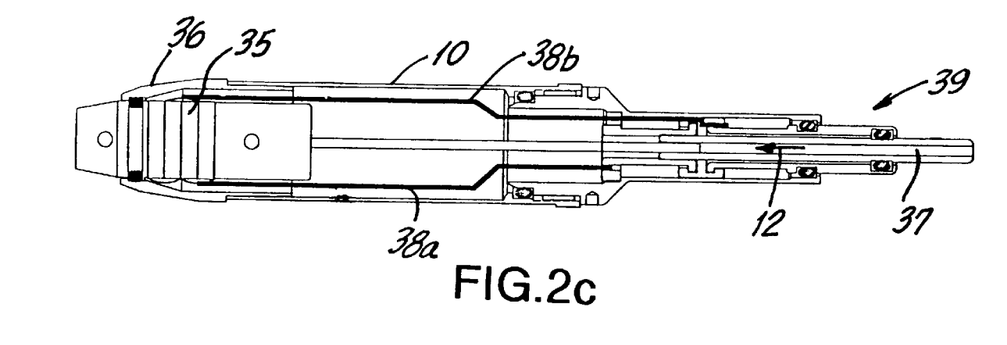
FIG. 2c is a cross-sectional view with the heating element removed to show the ultrasonic transducers.
Figure 2D:
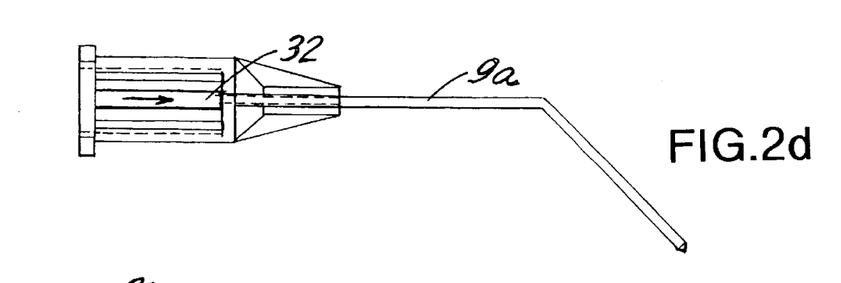
FIG. 2d is a cross-sectional view of an irrigator tip.
Figure 5:
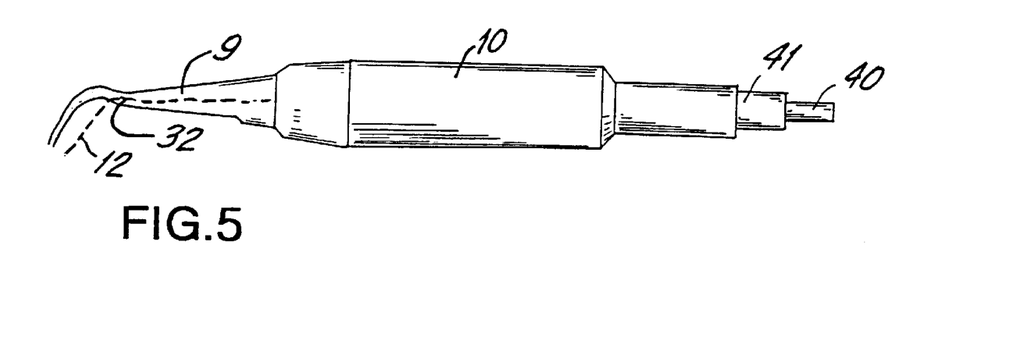
FIG. 5 is a side elevational view of a dental scaler handpiece with a scaling tip in accordance with the present invention.

Referring to FIG. 2c, a dedicated scaler handpiece 10a is shown which has an ultrasonic transducer 35, located in a forward portion 36 of the handpiece 10a. The ultrasonic transducer transmits vibration through the forward portion to an attached tip. In this embodiment, no internal heating element is used, and the irrigant 12 is supplied through an axial passage 37, primarily for cooling the scaler tip, as shown in FIG. 5. The transducer is connected by a pair of leads 38a and 38b to a connector portion 39 of the handpiece.

Irrigant liquid 12, electrical energy for the heating element 30 or 34 and electrical energy for the ultrasonic transducer 35 are all supplied to the handpiece 10 or 10a through the connector portion 39.

Referring again to FIG. 2a, the connector portion 39 includes a negative contact tip 40 and a positive contact shoulder 41. The connector portion is common to all handpieces to ease interchangeability, though described here relative to the handpiece 10. The axial irrigant inlet channel 28 extends through the negative contact tip 40, the negative contact tip acting as a carrier of irrigating fluid as well as a carrier of electricity. Thus, wires do not need to extend into the contact portion 39 reducing the overall diameter of the connection portion. The negative contact tip 40 and the positive contact shoulder 41 are preferably cylindrical in shape and coaxial to one another. An o-ring 42 provides electrical insulation between the negative contact tip 40 and the positive contact shoulder 41. Another o-ring 43 provides insulation between the positive shoulder 41 and the handpiece casing 44. These o-rings are made of a resilient polymer material which is substantially non-conductive.

Figure 3:
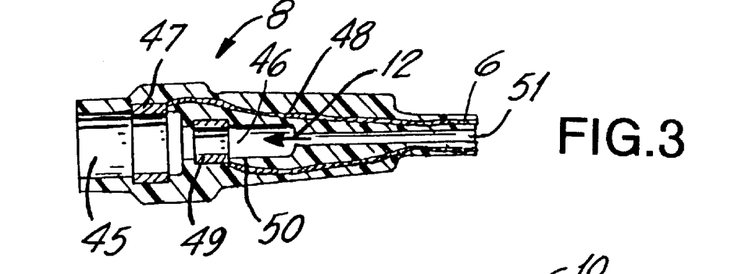
FIG. 3 is a cross-sectional illustration of a connector boot for a dental scaler in accordance with the present invention.

Referring to FIG. 3, the connector portion 39 of the handpiece 10 is connectable to the cable 6 through the resilient connector boot 8. The resilient boot 8 includes a first large diameter cylindrical passage 45 and a second smaller diameter cylindrical passage 46. When the connector end 39 is mated to the connector boot 8 (FIG. 4), the negative tip 40 fits within the smaller passage 46, and the positive shoulder 41 fits within the large diameter cylindrical passage 45. An annular positive electrical contact 47 is mounted in the large passage 45 and is connected to a positive lead wire 48, which extends through the cable 6 to the housing 2. Likewise, an annular negative electrical contact 49 is mounted in the smaller passage 46 and is connected to a negative lead wire 50, which extends through the cable 6 to the housing 2. Preferably these contacts engage the corresponding portions of the handpiece with an interference fit to assure electrical continuity. A water passage 51 extends through the cable 6 to supply irrigant liquid 12 to the scaler 5 through the axial irrigant inlet channel 28.

Figure 4:
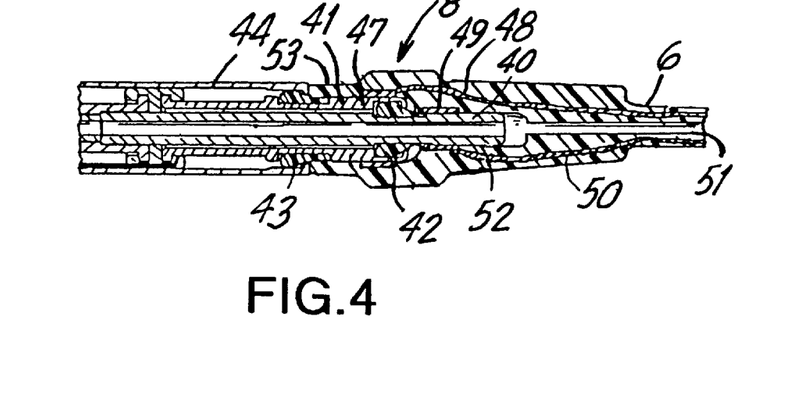
FIG. 4 is a cross-sectional illustration of a connection between the dental scaler handpiece of FIG. 2a and the connector boot of FIG. 3.

Referring to FIG. 4, the resilient boot 8 is shown engaged to the handpiece, the resilient portions of the boot 8 forming a first seal 52 around the negative tip 28 to prevent irrigant leakage, and a second seal 53 to electrically isolate the positive shoulder 41. Preferably, the connector 7 which connects the cable 6 to the housing 2 is identical to the connector boot 8, so that the ends are interchangeable. The housing would of course include an identical corresponding negative tip, a positive shoulder and an irrigant passage. FIG. 5 shows the scaler handpiece assembled to a tip, the irrigant 12 passing within the passage 32 in the tip shown in phantom.

Figure 6:
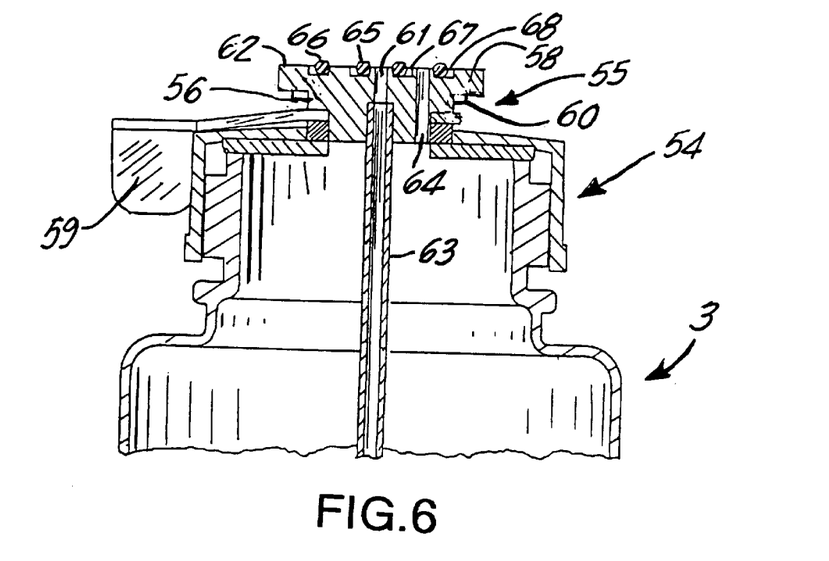
FIG. 6 is a cross sectional view of a reservoir bottle, cap, and mounting member assembly for a dental scaler system in accordance with the present invention.

Referring to FIG. 6, the irrigant supply bottle 3 includes a cap 54 with a mounting member 55 which mates with the docking assembly 25 on the housing. The mounting member 55 has a neck 56 having a pair of opposed alignment flanges 57 and a pair of opposed arcuate wings 58, best seen in FIG. 8a. A lever is incorporated with the neck, spaced beneath the wings. Beneath each wing is located a ramped surface 60, which will be described below. An irrigant liquid outlet 61 on an upper surface 62 of the mounting member 55 extends to a dip tube 63. A ventilation duct 64 also extends through the mounting member 55. An inner o-ring 65 and an outer o-ring 66 are located in grooves 67 and 68 respectively, and are concentric with one another for separating the irrigant liquid outlet 61 from the ventilation duct 64.

Figure 7:
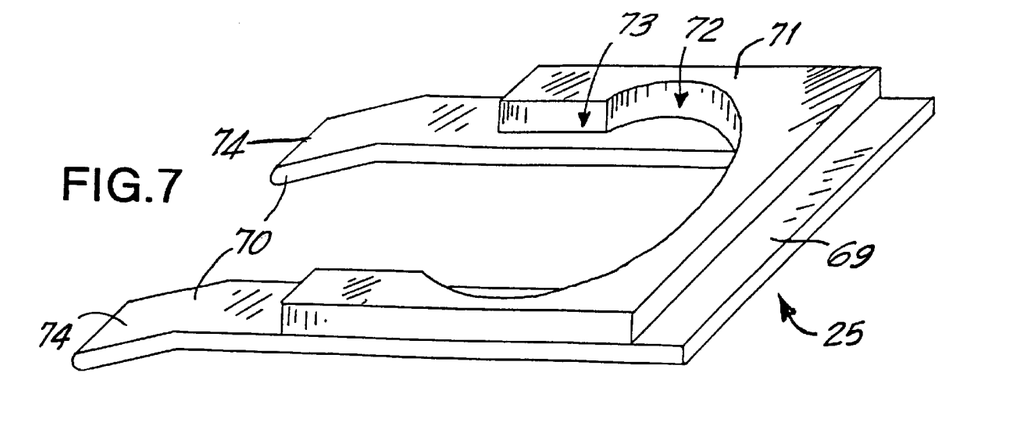
FIG. 7 is a perspective view of a receptacle assembly mateable with the mounting member of FIG. 6.

Referring to FIG. 7, the docking assembly 25 includes a fork 69 with tines 70, and a receiving member 71 which defines a circular bay 72 and an entry slot 73. A surface of the housing, to which the fork and receiving member are attached, completes the docking assembly, as will be described below. Preferably, the tines 71 are sloped and tapered at a forward portion 74 thereof to ease insertion of the mounting member 41, the tines received by the spacing in the neck 56 of the mounting member.

Figure 8A:
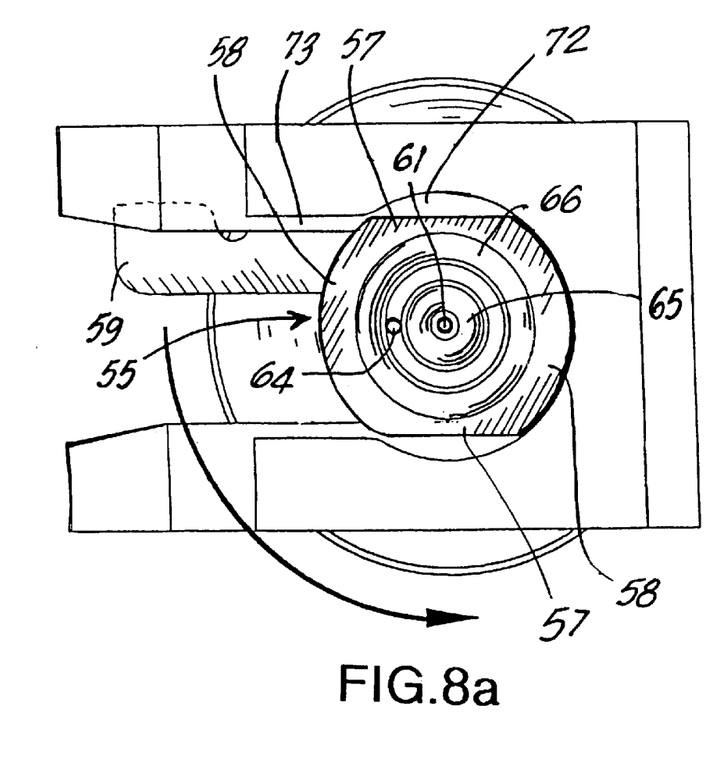
FIGS. 8a and 8b are plan views of progressive stages of mating the mounting member of FIG. 6 with the receptacle assembly of FIG. 7.

Referring to FIG. 8a, the mounting member 55 has an unlocked orientation wherein the wings 58 span along the tines 50. The pair of alignment flanges 57 are parallel to and received on the tines, allowing the mounting member to be slid along the slot 71, into the bay 72. The bay receives the mounting member therein, at which point the lever is used to rotate the mounting member so that the wings are fully received in the bay on the tines. As the wings move onto the tines, the ramped surfaces 60 beneath the wings engage the tines to force the top surface 62 of the mounting member into close engagement with a receiving surface on the housing, thereby compressing the o-rings to assure proper sealing. Thus, a quick quarter turn is all that is needed to mount and dismount the irrigant bottles. This allows a quick and easy removal or substitution of bottles, depending upon patient needs.

Figure 8B:
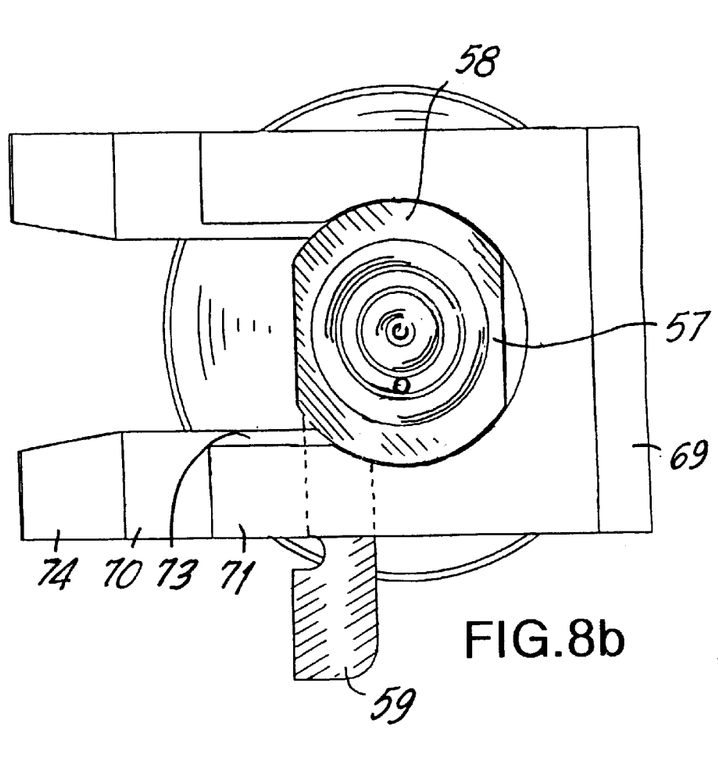

Once the mounting member 41 has been rotated into the locked orientation, the wings 58 engage the curved edges of the bay 72, and the mounting member 55 is prevented from sliding out of the bay 72 through the entry slot 73. Preferably, the bay 72 is circular in shape, and the wings 58 are arcs of a circle concentric with the circle of the bay 72 and slightly smaller in diameter, so that portions of the outer edges of the wings 58 engage the edge of the bay 72.

Figures 9A, 9B, 9C:
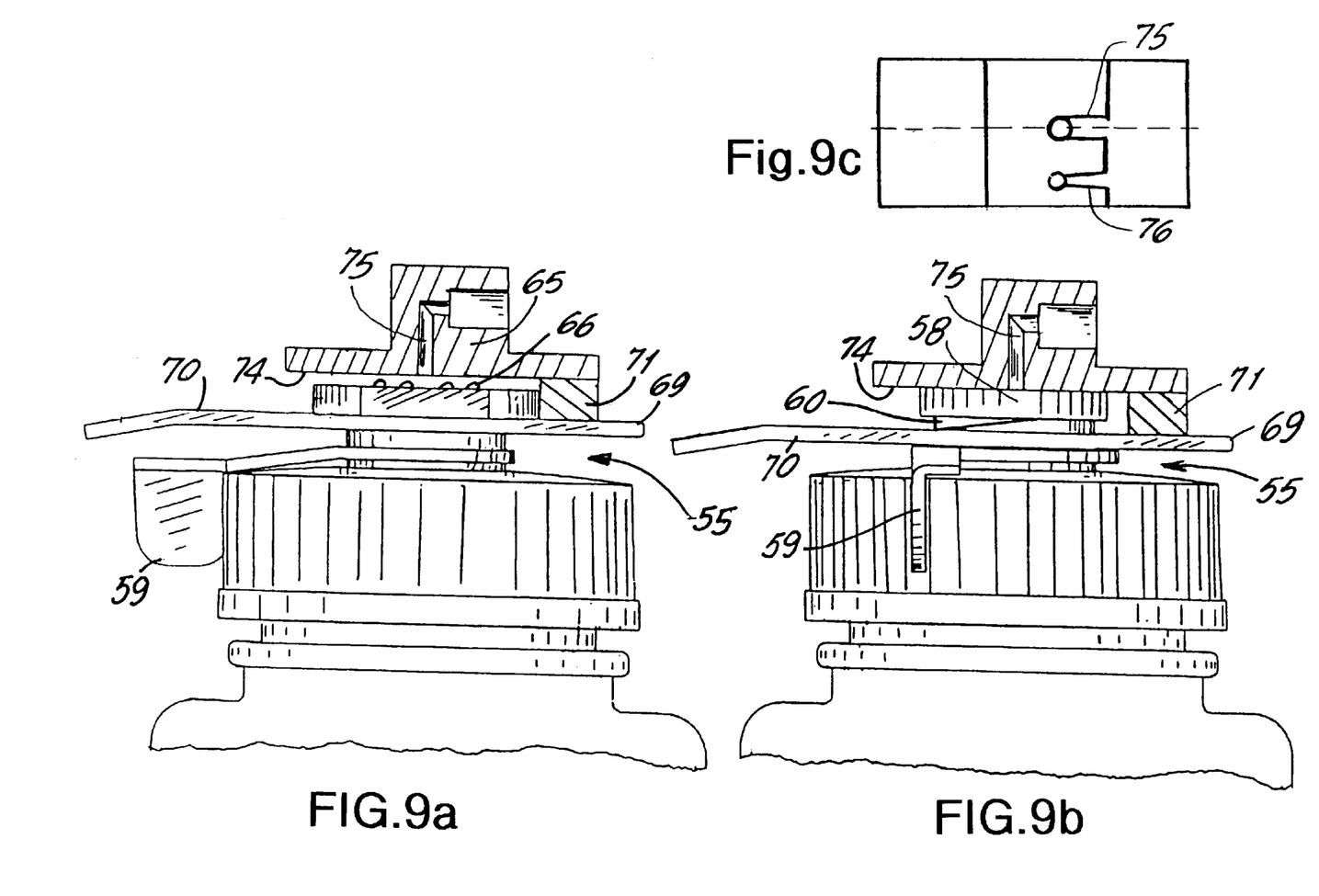
FIGS. 9a and 9b are side elevational views of progressive stages of mating the mounting member of FIG. 6 with the receptacle assembly of FIG. 7.
FIG. 9c is a top view of FIG. 9b.

Referring to FIG. 9a, b and c, a receiving surface 74 includes an irrigant port 75 and a vent port 76. The irrigant port 75 is centered over the bay 72 for alignment with the irrigant liquid outlet 61 of the mounting member 55 when the mounting member 55 is received in the bay. The vent port 76 is off center in a location corresponding to the spacing between the vent duct 64 and the irrigant outlet 61 of the mounting member. As the mounting member 55 is rotated using the lever 59 into the locked orientation, the ramped surfaces 60 on the underside of the wings 58 engage the tines 70 to force the mounting member 55 up against the receiving surface 74. The o-rings 65 and 66 are pressed against the receiving surface 74, sealing a fluid connections between the irrigant liquid outlet 61 and the irrigant port 75, and the connection between the vent duct 64 and the vent port 76.

Figure 10:
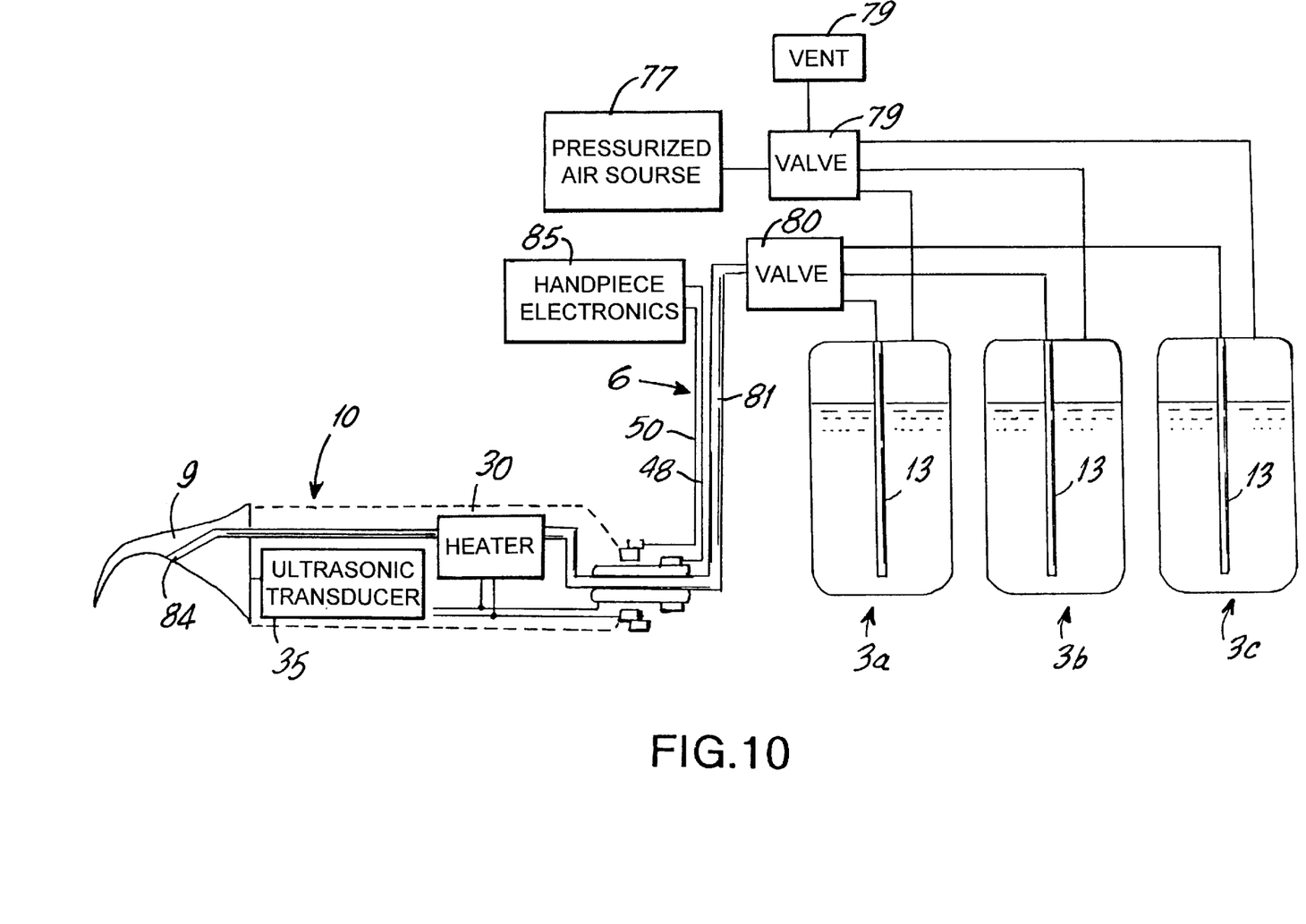
FIG. 10 is a schematic illustration of the dental scaler system.

Referring to FIG. 10, the electrical and fluid systems of the dental scaling system 1 are illustrated. In this figure, the illustrative scaler handpiece 10c performs both the scaler and irrigation function, with irrigant heating. A pressurized air source 77 is in communication with the irrigant bottles 3 through a valve 78 which can switch each bottle between being pressurized and vented through a vent 79. Selection of the vent button 20 (FIG. 1) causes the valve 78 to return the pressure inside the bottles 3 to atmospheric pressure. The pressurized air source 77 pumps pressurized air into the selected bottle 3, to cause irrigant to flow out of the dip tube 13 through a selector valve 80 into the cable 6, where the irrigant is transported through an irrigant passage 81 to the scaler handpiece 10, where the irrigant is heated by the heater 30 and expelled through an irrigant outlet 84 in the scaler tip 9. Handpiece control electronics 85 control the electrical energy provided to the heater 30 and the ultrasonic transducer 35. The handpiece electronics 85 are connected through the connector 7 (FIG. 1) to the positive and negative lead wires 48 and 50 of the cable 6. The various switches and controls described relative to the scaler are actuated through the handpiece electronics 85 and these are conventional within the art.

The dental scaler system also includes, within the electronic package, novel means for monitoring tip wear. The electronics package includes means for monitoring the resonance frequency changes in the tip, comparing the initial resonance frequency of the tip when used to the tip as it ages. When the resonance frequency reaches an upper limit, an error signal is generated which activates a switch, initiating either a visual or audible signal so that the user will know the tip must be replaced.

Figure 11:
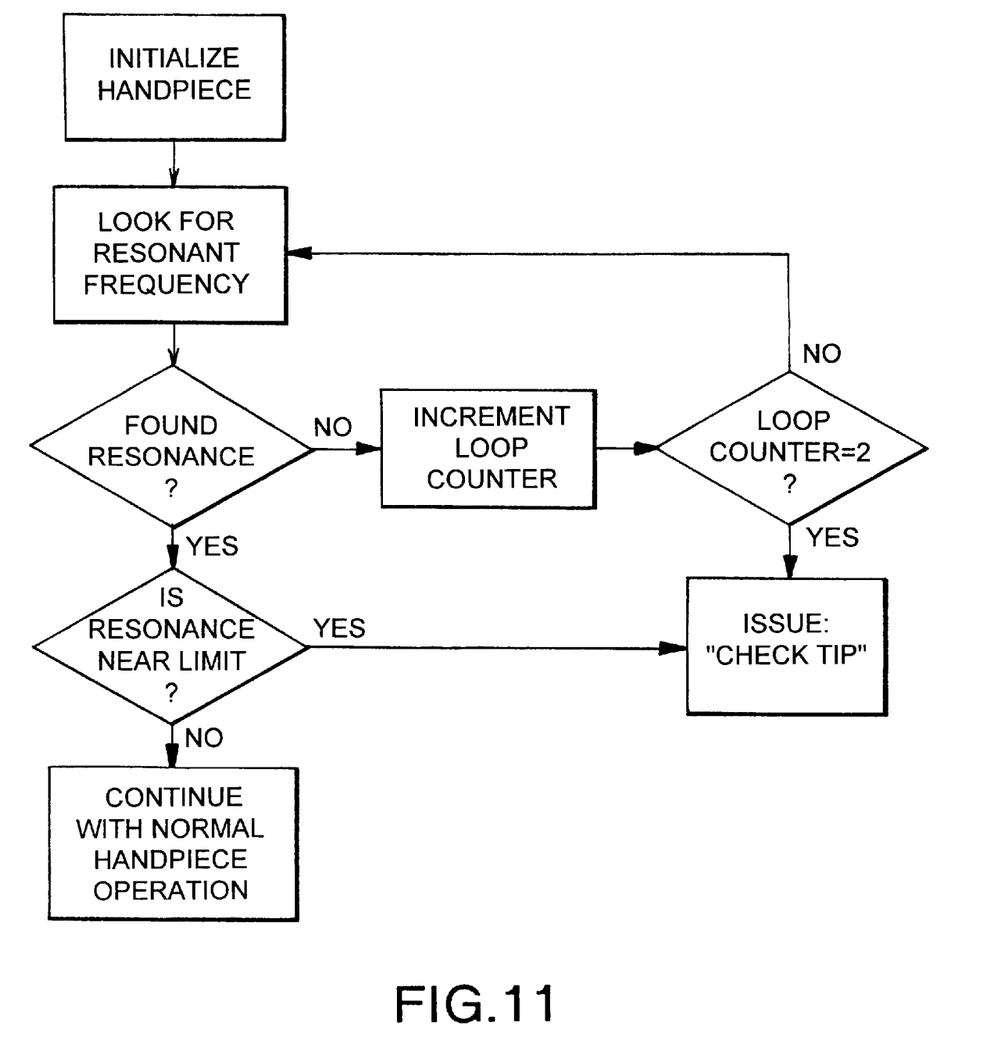
FIG. 11 is a block diagram of the electronics used in a dental scaler system in accordance with the present invention.

Referring to FIG. 11, when a tip is placed in the hand piece and the ultrasonic transducer is powered, a frequency analyzer performs a scan over a prescribed frequency range, typically from about 40 to 50 Khz when using a titanium tip. The range is generally chosen to correspond to a working frequency range of the tip. By scanning over the frequency range, the resonance frequency of the tip is located. If the resonance frequency is not found, a second scan is performed through an increment loop counter. If after the second scan, the resonance frequency is not found, a "check tip" signal is initiated.

If the resonance frequency falls within the range of about 40 to 47 Khz, the handpiece and tip operate normally. However, if the resonance frequency is either out of the full scan range, or over a prescribed limit such as 48 Khz, then the "check tip" signal is initiated. If desired, the transducer power can be terminated pending replacement of the tip. Utilizing such a system optimizes scaler performance by timely changing of a worn tip.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A dental scaling system comprising:

a handpiece, a tip mounted at a forward end of the handpiece, an irrigant outlet in the tip, the handpiece having an irrigant inlet and an irrigant passage passing therethrough connected to the irrigant outlet;

means for releasably attaching the handpiece to an irrigant supply and a power supply, an irrigant passage extending therethrough, the means for attaching having a first end attachable to the handpiece;

an irrigant supply bottle containing an irrigant;

a housing on which the irrigant supply bottle is releasably attached, the irrigant supply bottle having means for releasably mounting to the housing, the housing having means for engaging a second end of the attaching means, the housing having means for transferring the irrigant from the irrigant supply bottle through the attaching means to the tip, and having controls for providing power thereto; and, means for monitoring tip wear disposed in the housing.

2. The dental scaling system of claim 1 wherein the attaching means is a cable which includes a first electrical wire and a second electrical wire for transferring electrical energy from the housing to the handpiece.

3. The dental scaling system of claim 1 wherein the tip is a scaling tip.

4. The dental scaling system of claim 1 wherein the tip is an irrigation tip.

5. The dental scaling system of claim 1 wherein an ultrasonic transducer is located in the handpiece.

6. The dental scaler system of claim 5 further comprising control means for adjusting a power level of the ultrasonic transducer and for adjusting a rate of flow of irrigant to the tip.

7. The dental scaler of claim 5 further comprising a foot pedal for activating the ultrasonic transducer.

8. The dental scaling system of claim 1 wherein each end of the attachment means includes a resilient boot, the boot including:

a first cylindrical passage having a first passage diameter extending axially into the boot;

a second cylindrical passage coaxial with the first passage and having a second passage diameter smaller than the first passage diameter;

a first electrical contact on an inner surface of the first passage, the first electrical contact being electrically connected to the first electrical wire; and a second electrical contact on an inner surface of the second passage, the second electrical contact being electrically connected to the second electrical wire;

the irrigant passage of the attachment means being in fluid communication with the second passage.

9. The dental scaling system of claim 1 wherein the handpiece has a connector portion having a cylindrical shoulder portion and a cylindrical tip portion adjacent thereto coaxial with the shoulder portion, the tip portion diameter being smaller than the shoulder portion diameter, the irrigant inlet being in an end of the cylindrical tip portion.

10. The dental scaling system of claim 9 wherein means for electrical isolation are located in the handpiece between the contact tip and the contact shoulder.

11. The dental scaling system of claim 10 wherein the electrical isolation means comprise resilient o-rings.

12. The dental scaling system of claim 1 wherein the irrigant bottle includes a cap having a mounting member, the mounting member having first and second passages extending therethrough, and having an irrigant liquid outlet on an upper surface thereof, the mounting member further having a neck portion beneath a pair of opposed wings, and a pair of opposed alignment flanges, each of the wings having a ramp on a lower surface thereof.

13. The dental scaling system of claim 1 wherein the housing includes a docking assembly for receiving the irrigant supply bottle, the docking assembly including:

a fork with a pair of tines spaced to receive an irrigant bottle thereon;

a receiving surface having an irrigant port and a vent port; and a receiving member mounted between the fork and the receiving surface, the receiving member defining a bay and an entry slot for receiving the means for mounting the irrigant bottle therein.

14. The dental scaling system of claim 1 and wherein the means for mounting the irrigant bottle has an unlocked orientation and a locked orientation, the means for mounting being rotatable between the locked orientation and the unlocked orientation in one quarter turn.

15. The dental scaling system of claim 1 wherein the means for mounting the irrigant bottle includes seal means on an upper surface thereof for preventing leakage as the irrigant passes out of the bottle.

16. The dental scaling system of claim 15 wherein the seal means comprise an inner o-ring and an outer o-ring, the inner and outer o-rings being concentric, the irrigant liquid outlet being positioned within the inner o-ring, the mounting member further including a bottle vent communicating between the inside of the bottle and the upper surface of the mounting member, the bottle vent being positioned between the inner o-ring and the outer o-ring.

17. The dental scaling system of claim 1 wherein the transfer means deliver pressurized air to the irrigant bottle to displace the irrigant therefrom.

18. The dental scaler system of claim 1 wherein the means for monitoring include a frequency analyzer to monitor a resonance frequency of the tip and to issue a signal when the resonance frequency exceeds a predetermined limit.

19. The dental scaler of claim 1 further comprising a foot pedal for activating transfer means.

20. The dental scaling system of claim 1 further comprising means for heating the irrigant as it passes through the irrigant passage in the handpiece.

21. The dental scaler of claim 20 wherein the heating means is an electrical heating element disposed adjacent to the irrigant passage.

22. A dental scaling system comprising:

a scaling instrument having a handpiece, a scaling tip at a first end of the handpiece, an ultrasonic transducer in the handpiece connected to the scaling tip, an irrigant outlet in the scaling tip, and an irrigant inlet opening to an irrigant passage extending through the handpiece, the irrigant passage acting as a negative power conductor in the handpiece to reduce handpiece diameter;

a cable releasably attached at a first end thereof to the handpiece, the cable having an irrigant passage and first and second wires extending therethrough, a resilient boot at least a first end thereof, the boot including a first cylindrical passage having a first passage diameter extending axially into the boot, a second cylindrical passage coaxial with the first passage and having a second passage diameter smaller than the first passage diameter, a first electrical contact on an inner surface of the first passage connected to the first wire, and a second electrical contact on an inner surface of the second passage connected to the second electrical wire, the irrigant passage of the cable being in fluid communication with the second passage;

the cable being attachable at a second end thereof with a source of irrigant liquid and electrical energy.

23. The dental scaling system of claim 22 wherein the handpiece has a connector portion having a cylindrical contact shoulder having a shoulder diameter and a cylindrical contact tip coaxial with the shoulder having a tip diameter, the tip diameter being smaller than the shoulder diameter, the irrigant inlet being in the cylindrical tip.

24. The dental scaling system of claim 23 wherein the shoulder diameter is approximately equal to the first passage diameter and the tip diameter is approximately equal to the second passage diameter.

25. The dental scaling system of claim 22 further comprising means for heating the irrigant as it passes through the irrigant passage in the handpiece.

26. The dental scaler of claim 22 wherein the heating means is an electrical heating element disposed adjacent to the irrigant passage.

27. The dental scaling system of claim 22 wherein means for electrical isolation are located in the handpiece are located in the handpiece between the contact tip and the contact shoulder.

28. The dental scaling system of claim 22 wherein the electrical isolation means comprise resilient o-rings.

29. A method for scaling tooth surfaces comprising:

providing a handpiece, a tip mounted at a forward end of the handpiece, an irrigant outlet in the tip, the handpiece having an irrigant inlet and an irrigant passage passing therethrough connected to the irrigant outlet;

providing means for releasably attaching the handpiece to an irrigant supply and a power supply, an irrigant passage extending therethrough, the means for attaching having a first end attachable to the handpiece;

providing an irrigant supply bottle containing an irrigant;

providing a housing on which the irrigant supply bottle is releasably attached, the irrigant supply bottle having means for releasably mounting to the housing, the housing having means for engaging a second end of the attaching means, the housing having means for transferring the irrigant from the irrigant supply bottle through the attaching means to the tip, and having controls for providing power thereto;

connecting the attaching means to the handpiece and to the housing;

selectively supply power to the handpiece;

using the tip to scale tooth surfaces, and while supplying irrigant from the irrigant supply bottle to the tip; and, monitoring a resonance frequency of the tip and issuing a signal when a preselected upper frequency limit is exceeded.

30. The method of claim 29 further comprising providing at least two irrigant supply bottles, providing a medicament in at least one of the bottles and selectably supplying the medicament to surfaces in the mouth.

31. The method of claim 29 further comprising heating the irrigant as it passes through the handpiece.

32. The method claim 29 wherein the means for mounting the irrigant bottle has an unlocked orientation and a locked orientation, and further comprising placing the irrigant supply bottle on the housing and rotating the mounting member one quarter turn between the unlocked orientation and the locked orientation.

33. The method of claim 29 further comprising providing an ultrasonic transducer in the handpiece.

34. A dental scaling system comprising:

a handpiece, a tip mounted at a forward end of the handpiece, an irrigant outlet in the tip, the handpiece having an irrigant inlet and an irrigant passage passing therethrough connected to the irrigant outlet;

means for releasably attaching the handpiece to an irrigant supply and a power supply, an irrigant passage extending therethrough, the means for attaching having a first end attachable to the handpiece;

an irrigant supply bottle containing an irrigant; and a housing on which the irrigant supply bottle is releasably attached, the irrigant supply bottle having means for releasably mounting to the housing, the housing having means for engaging a second end of the attaching means, the housing having means for transferring the irrigant from the irrigant supply bottle through the attaching means to the tip, and having controls for providing power thereto;

wherein each end of the attachment means includes a resilient boot, the boot including:

a first cylindrical passage having a first passage diameter extending axially into the boot;

a second cylindrical passage coaxial with the first passage and having a second passage diameter smaller than the first passage diameter;

a first electrical contact on an inner surface of the first passage, the first electrical contact being electrically connected to the first electrical wire; and a second electrical contact on an inner surface of the second passage, the second electrical contact being electrically connected to the second electrical wire;

the irrigant passage of the attachment means being in fluid communication with the second passage.

35. The dental scaling system of claim 34 wherein the attaching means is a cable which includes a first electrical wire and a second electrical wire for transferring electrical energy from the housing to the handpiece.

36. The dental scaling system of claim 34 wherein the tip is a scaling tip.

37. The dental scaling system of claim 34 wherein the tip is an irrigation tip.

38. The dental scaling system of claim 34 wherein an ultrasonic transducer is located in the handpiece.

39. The dental scaler system of claim 38 further comprising control means for adjusting a power level of the ultrasonic transducer and for adjusting a rate of flow of irrigant to the tip.

40. The dental scaler of claim 38 further comprising a foot pedal for activating the ultrasonic transducer.

41. The dental scaling system of claim 34 wherein the handpiece has a connector portion having a cylindrical shoulder portion and a cylindrical tip portion adjacent thereto coaxial with the shoulder portion, the tip portion diameter being smaller than the shoulder portion diameter, the irrigant inlet being in an end of the cylindrical tip portion.

42. The dental scaling system of claim 41 wherein means for electrical isolation are located in the handpiece between the contact tip and the contact shoulder.

43. The dental scaling system of claim 34 wherein the irrigant bottle includes a cap having a mounting member, the mounting member having first and second passages extending therethrough, and having an irrigant liquid outlet on an upper surface thereof, the mounting member further having a neck portion beneath a pair of opposed wings, and a pair of opposed alignment flanges, each of the wings having a ramp on a lower surface thereof.

44. The dental scaling system of claim 34 wherein the housing includes a docking assembly for receiving the irrigant supply bottle, the docking assembly including:

a fork with a pair of tines spaced to receive an irrigant bottle thereon;

a receiving surface having an irrigant port and a vent port; and a receiving member mounted between the fork and the receiving surface, the receiving member defining a bay and an entry slot for receiving the means for mounting the irrigant bottle therein.

45. The dental scaling system of claim 34 and wherein the means for mounting the irrigant bottle has an unlocked orientation and a locked orientation, the means for mounting being rotatable between the locked orientation and the unlocked orientation in one quarter turn.

46. The dental scaling system of claim 34 wherein the means for mounting the irrigant bottle includes seal means on an upper surface thereof for preventing leakage as the irrigant passes out of the bottle.

47. The dental scaling system of claim 46 wherein the seal means comprise an inner o-ring and an outer o-ring, the inner and outer o-rings being concentric, the irrigant liquid outlet being positioned within the inner o-ring, the mounting member further including a bottle vent communicating between the inside of the bottle and the upper surface of the mounting member, the bottle vent being positioned between the inner o-ring and the outer o-ring.

48. The dental scaling system of claim 34 wherein the transfer means deliver pressurized air to the irrigant bottle to displace the irrigant therefrom.

49. The dental scaling system of claim 34 further comprising means for monitoring tip wear disposed in the housing.

50. The dental scaler system of claim 49 wherein the means for monitoring include a frequency analyzer to monitor a resonance frequency of the tip and to issue a signal when the resonance frequency exceeds a predetermined limit.

51. The dental scaler of claim 34 further comprising a foot pedal for activating the irrigant transfer means.

52. The dental scaling system of claim 34 further comprising means for heating the irrigant as it passes through the irrigant passage in the handpiece.

53. The dental scaler of claim 52 wherein the heating means is an electrical heating element disposed adjacent to the irrigant passage.

54. The dental scaling system of claim 34 wherein the electrical isolation means comprise resilient o-rings.

55. A dental scaling system comprising:
a handpiece, a tip mounted at a forward end of the handpiece, an irrigant outlet in the tip, the handpiece having an irrigant inlet and an irrigant passage passing therethrough connected to the irrigant outlet;
means for releasably attaching the handpiece to an irrigant supply and a power supply, an irrigant passage extending therethrough, the means for attaching having a first end attachable to the handpiece;
an irrigant supply bottle containing an irrigant;
a housing on which the irrigant supply bottle is releasably attached, the irrigant supply bottle having means for releasably mounting to the housing, the housing having means for engaging a second end of the attaching means, the housing having means for transferring the irrigant from the irrigant supply bottle through the attaching means to the tip, and having controls for providing power thereto; and
the irrigant supply bottle includes a cap having a mounting member, the mounting member having first and second passages extending therethrough, and having an irrigant liquid outlet on an upper surface thereof, the mounting member further having a neck portion beneath a pair of opposed wings, and a pair of opposed alignment flanges, each of the wings having a ramp on a lower surface thereof.

56. The dental scaling system of claim 55 wherein the attaching means is a cable which includes a first electrical wire and a second electrical wire for transferring electrical energy from the housing to the handpiece.

57. The dental scaling system of claim 55 wherein the tip is a scaling tip.

58. The dental scaling system of claim 55 wherein the tip is an irrigation tip.

59. The dental scaling system of claim 55 wherein an ultrasonic transducer is located in the handpiece.

60. The dental scaler system of claim 59 further comprising control means for adjusting a power level of the ultrasonic transducer and for adjusting a rate of flow of irrigant to the tip.

61. The dental scaler of claim 59 further comprising a foot pedal for activating the ultrasonic transducer.

62. The dental scaling system of claim 55 wherein the handpiece has a connector portion having a cylindrical shoulder portion and a cylindrical tip portion adjacent thereto coaxial with the shoulder portion, the tip portion diameter being smaller than the shoulder portion diameter, the irrigant inlet being in an end of the cylindrical tip portion.

63. The dental scaling system of claim 62 wherein means for electrical isolation are located in the handpiece between the contact tip and the contact shoulder.

64. The dental scaling system of claim 55 wherein the housing includes a docking assembly for receiving the irrigant supply bottle, the docking assembly including:
a fork with a pair of tines spaced to receive an irrigant bottle thereon;
a receiving surface having an irrigant port and a vent port; and
a receiving member mounted between the fork and the receiving surface, the receiving member defining a bay and an entry slot for receiving the means for mounting the irrigant bottle therein.

65. The dental scaling system of claim 55 and wherein the means for mounting the irrigant bottle has an unlocked orientation and a locked orientation, the means for mounting being rotatable between the locked orientation and the unlocked orientation in one quarter turn.

66. The dental scaling system of claim 55 wherein the means for mounting the irrigant bottle includes seal means on an upper surface thereof for preventing leakage as the irrigant passes out of the bottle.

67. The dental scaling system of claim 66 wherein the seal means comprise an inner o-ring and an outer o-ring, the inner and outer o-rings being concentric, the irrigant liquid outlet being positioned within the inner o-ring, the mounting member further including a bottle vent communicating between the inside of the bottle and the upper surface of the mounting member, the bottle vent being positioned between the inner o-ring and the outer o-ring.

68. The dental scaling system of claim 55 wherein the transfer means deliver pressurized air to the irrigant bottle to displace the irrigant therefrom.

69. The dental scaling system of claim 55 further comprising means for monitoring tip wear disposed in the housing.

70. The dental scaler system of claim 69 wherein the means for monitoring include a frequency analyzer to monitor a resonance frequency of the tip and to issue a signal when the resonance frequency exceeds a predetermined limit.

71. The dental scaler of claim 55 further comprising a foot pedal for activating the irrigant transfer means.

72. The dental scaling system of claim 55 further comprising means for heating the irrigant as it passes through the irrigant passage in the handpiece.

73. The dental scaler of claim 72 wherein the heating means is an electrical heating element disposed adjacent to the irrigant passage.

74. The dental scaling system of claim 55 wherein the electrical isolation means comprise resilient o-rings.

75. A dental scaling system comprising:
a handpiece, a tip mounted at a forward end of the handpiece, an irrigant outlet in the tip, the handpiece having an irrigant inlet and an irrigant passage passing therethrough connected to the irrigant outlet;
means for releasably attaching the handpiece to an irrigant supply and a power supply, an irrigant passage extending therethrough, the means for attaching having a first end attachable to the handpiece;

an irrigant supply bottle containing an irrigant;

a housing on which the irrigant supply bottle is releasably attached, the irrigant supply bottle having means for releasably mounting to the housing, the housing having means for engaging a second end of the attaching means, the housing having means for transferring the irrigant from the irrigant supply bottle through the attaching means to the tip, and having controls for providing power thereto; and wherein the housing includes a docking assembly for receiving the irrigant supply bottle, the docking assembly including:

a fork with a pair of tines spaced to receive an irrigant bottle thereon;

a receiving surface having an irrigant port and a vent port; and a receiving member mounted between the fork and the receiving surface, the receiving member defining a bay and an entry slot for receiving the means for mounting the irrigant bottle therein.

76. The dental scaling system of claim 75 wherein the attaching means is a cable which includes a first electrical wire and a second electrical wire for transferring electrical energy from the housing to the handpiece.

77. The dental scaling system of claim 75 wherein the tip is a scaling tip.

78. The dental scaling system of claim 75 wherein the tip is an irrigation tip.

79. The dental scaling system of claim 75 wherein an ultrasonic transducer is located in the handpiece.

80. The dental scaler system of claim 79 further comprising control means for adjusting a power level of the ultrasonic transducer and for adjusting a rate of flow of irrigant to the tip.

81. The dental scaler of claim 79 further comprising a foot pedal for activating the ultrasonic transducer.

82. The dental scaling system of claim 75 wherein the handpiece has a connector portion having a cylindrical shoulder portion and a cylindrical tip portion adjacent thereto coaxial with the shoulder portion, the tip portion diameter being smaller than the shoulder portion diameter, the irrigant inlet being in an end of the cylindrical tip portion.

83. The dental scaling system of claim 82 wherein means for electrical isolation are located in the handpiece between the contact tip and the contact shoulder.

84. The dental scaling system of claim 75 wherein the irrigant bottle includes a cap having a mounting member, the mounting member having first and second passages extending therethrough, and having an irrigant liquid outlet on an upper surface thereof, the mounting member further having a neck portion beneath a pair of opposed wings, and a pair of opposed alignment flanges, each of the wings having a ramp on a lower surface thereof.

85. The dental scaling system of claim 75 and wherein the means for mounting the irrigant bottle has an unlocked orientation and a locked orientation, the means for mounting being rotatable between the locked orientation and the unlocked orientation in one quarter turn.

86. The dental scaling system of claim 75 wherein the means for mounting the irrigant bottle includes seal means on an upper surface thereof for preventing leakage as the irrigant passes out of the bottle.

87. The dental scaling system of claim 86 wherein the seal means comprise an inner o-ring and an outer o-ring, the inner and outer o-rings being concentric, the irrigant liquid outlet being positioned within the inner o-ring, the mounting member further including a bottle vent communicating between the inside of the bottle and the upper surface of the mounting member, the bottle vent being positioned between the inner o-ring and the outer o-ring.

88. The dental scaling system of claim 75 wherein the transfer means deliver pressurized air to the irrigant bottle to displace the irrigant therefrom.

89. The dental scaling system of claim 75 further comprising means for monitoring tip wear disposed in the housing.

90. The dental scaler system of claim 89 wherein the means for monitoring include a frequency analyzer to monitor a resonance frequency of the tip and to issue a signal when the resonance frequency exceeds a predetermined limit.

91. The dental scaler of claim 75 further comprising a foot pedal for activating the irrigant transfer means.

92. The dental scaling system of claim 75 further comprising means for heating the irrigant as it passes through the irrigant passage in the handpiece.

93. The dental scaler of claim 92 wherein the heating means is an electrical heating element disposed adjacent to the irrigant passage.

94. The dental scaling system of claim 75 wherein the electrical isolation means comprise resilient o-rings.

95. A dental scaling system comprising:

a handpiece, a tip mounted at a forward end of the handpiece, an irrigant outlet in the tip, the handpiece having an irrigant inlet and an irrigant passage passing therethrough connected to the irrigant outlet;

means for releasably attaching the handpiece to an irrigant supply and a power supply, an irrigant passage extending therethrough, the means for attaching having a first end attachable to the handpiece;

an irrigant supply bottle containing an irrigant;

a housing on which the irrigant supply bottle is releasably attached, the irrigant supply bottle having means for releasably mounting to the housing, the housing having means for engaging a second end of the attaching means, the housing having means for transferring the irrigant from the irrigant supply bottle through the attaching means to the tip, having controls for providing power thereto; and wherein the means for mounting the irrigant bottle includes seal means on an upper surface thereof for preventing leakage as the irrigant passes out of the bottle, the seal means being an inner o-ring and an outer o-ring, the inner and outer o-rings being concentric, the irrigant liquid outlet being positioned within the inner o-ring, the mounting member further including a bottle vent communicating between the inside of the bottle and the upper surface of the mounting member, the bottle vent being positioned between the inner o-ring and the outer o-ring.

96. The dental scaling system of claim 95 wherein the attaching means is a cable which includes a first electrical wire and a second electrical wire for transferring electrical energy from the housing to the handpiece.

97. The dental scaling system of claim 95 wherein the tip is a scaling tip.

98. The dental scaling system of claim 95 wherein the tip is an irrigation tip.

99. The dental scaling system of claim 95 wherein an ultrasonic transducer is located in the handpiece.

100. The dental scaler system of claim 99 further comprising control means for adjusting a power level of the ultrasonic transducer and for adjusting a rate of flow of irrigant to the tip.

101. The dental scaler of claim 99 further comprising a foot pedal for activating the ultrasonic transducer.

102. The dental scaling system of claim 95 wherein the handpiece has a connector portion having a cylindrical shoulder portion and a cylindrical tip portion adjacent thereto coaxial with the shoulder portion, the tip portion diameter being smaller than the shoulder portion diameter, the irrigant inlet being in an end of the cylindrical tip portion.

103. The dental scaling system of claim 102 wherein means for electrical isolation are located in the handpiece between the contact tip and the contact shoulder.

104. The dental scaling system of claim 95 wherein the irrigant bottle includes a cap having a mounting member, the mounting member having first and second passages extending therethrough, and having an irrigant liquid outlet on an upper surface thereof, the mounting member further having a neck portion beneath a pair of opposed wings, and a pair of opposed alignment flanges, each of the wings having a ramp on a lower surface thereof.

105. The dental scaling system of claim 95 wherein the housing includes a docking assembly for receiving the irrigant supply bottle, the docking assembly including:

a fork with a pair of tines spaced to receive an irrigant bottle thereon;

a receiving surface having an irrigant port and a vent port; and a receiving member mounted between the fork and the receiving surface, the receiving member defining a bay and an entry slot for receiving the means for mounting the irrigant bottle therein.

106. The dental scaling system of claim 95 and wherein the means for mounting the irrigant bottle has an unlocked orientation and a locked orientation, the means for mounting being rotatable between the locked orientation and the unlocked orientation in one quarter turn.

107. The dental scaling system of claim 106 wherein the seal means comprise an inner o-ring and an outer o-ring, the inner and outer o-rings being concentric, the irrigant liquid outlet being positioned within the inner o-ring, the mounting member further including a bottle vent communicating between the inside of the bottle and the upper surface of the mounting member, the bottle vent being positioned between the inner o-ring and the outer o-ring.

108. The dental scaling system of claim 95 wherein the transfer means deliver pressurized air to the irrigant bottle to displace the irrigant therefrom.

109. The dental scaling system of claim 95 further comprising means for monitoring tip wear disposed in the housing.

110. The dental scaler system of claim 109 wherein the means for monitoring include a frequency analyzer to monitor a resonance frequency of the tip and to issue a signal when the resonance frequency exceeds a predetermined limit.

111. The dental scaler of claim 95 further comprising a foot pedal for activating the irrigant transfer means.

112. The dental scaling system of claim 95 further comprising means for heating the irrigant as it passes through the irrigant passage in the handpiece.

113. The dental scaler of claim 112 wherein the heating means is an electrical heating element disposed adjacent to the irrigant passage.

114. The dental scaling system of claim 95 wherein the electrical isolation means comprise resilient o-rings.

115. A method for scaling tooth surfaces comprising:

providing a handpiece, a tip mounted at a forward end of the handpiece, an irrigant outlet in the tip, the handpiece having an irrigant inlet and an irrigant passage passing therethrough connected to the irrigant outlet;

providing means for releasably attaching the handpiece to an irrigant supply and a power supply, an irrigant passage extending therethrough, the means for attaching having a first end attachable to the handpiece;

providing an irrigant supply bottle containing an irrigant;

providing a housing on which the irrigant supply bottle is releasably attached, the irrigant supply bottle having means for releasably mounting to the housing, the housing having means for engaging a second end of the attaching means, the housing having means for transferring the irrigant from the irrigant supply bottle through the attaching means to the tip, and having controls for providing power thereto; and connecting the attaching means to the handpiece and to the housing;

selectively supplying power to the handpiece;

using the tip to scale tooth surfaces, and while supplying irrigant from the irrigant supply bottle to the tip; and wherein the means for mounting the irrigant bottle has an unlocked orientation and a locked orientation, and further comprising placing the irrigant supply bottle on the housing and rotating the mounting member one quarter turn between the unlocked orientation and the locked orientation.

116. The method of claim 115 further comprising providing at least two irrigant supply bottles, providing a medicament in at least one of the bottles and selectably supplying the medicament to surfaces in the mouth.

117. The method of claim 115 further comprising heating the irrigant as it passes through the handpiece.

118. The method of claim 115 further comprising monitoring a resonance frequency of the tip and issuing a signal when a preselected upper frequency limit is exceeded.

119. The method of claim 115 further comprising providing an ultrasonic transducer in the handpiece.

* * * * *